[redacted]

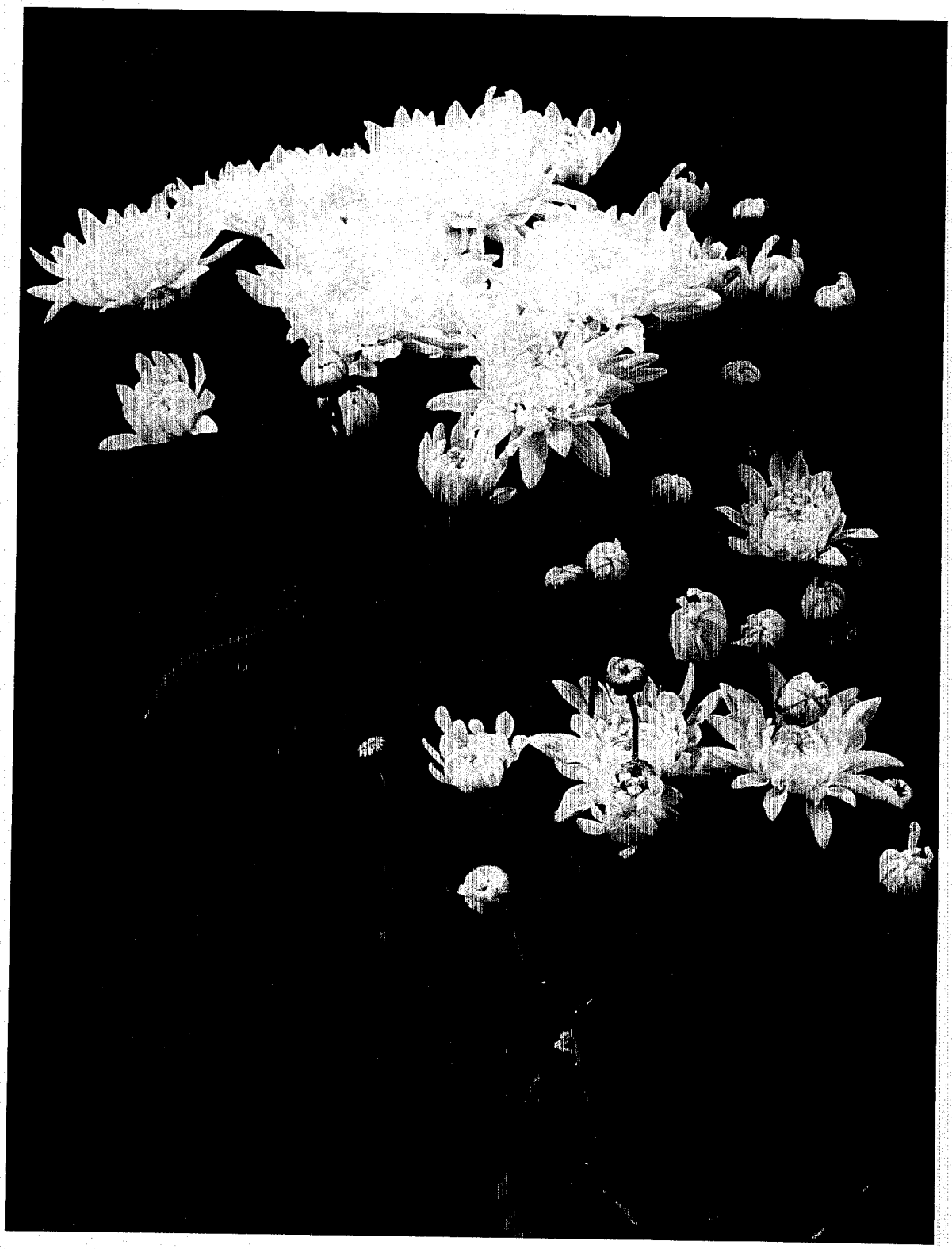

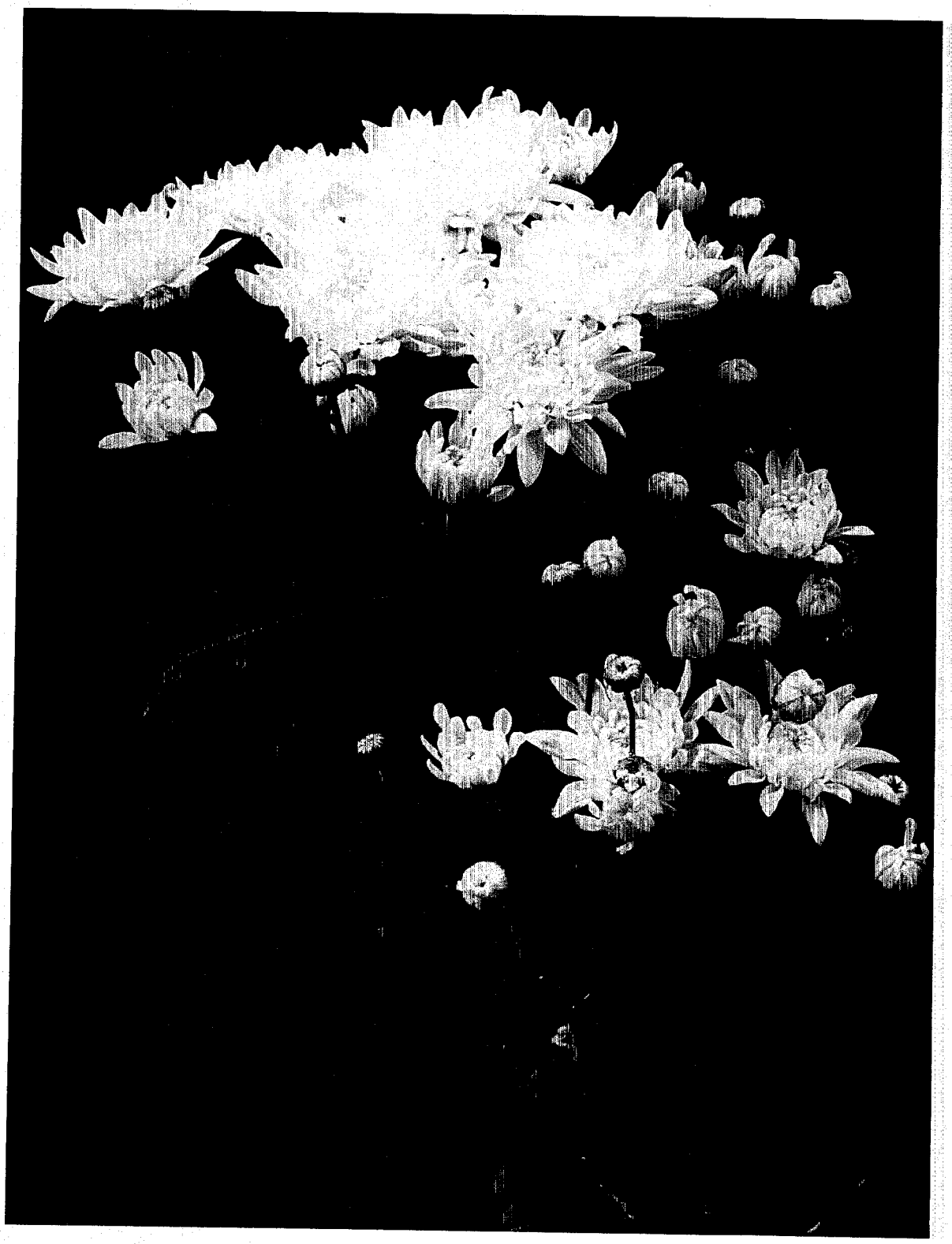

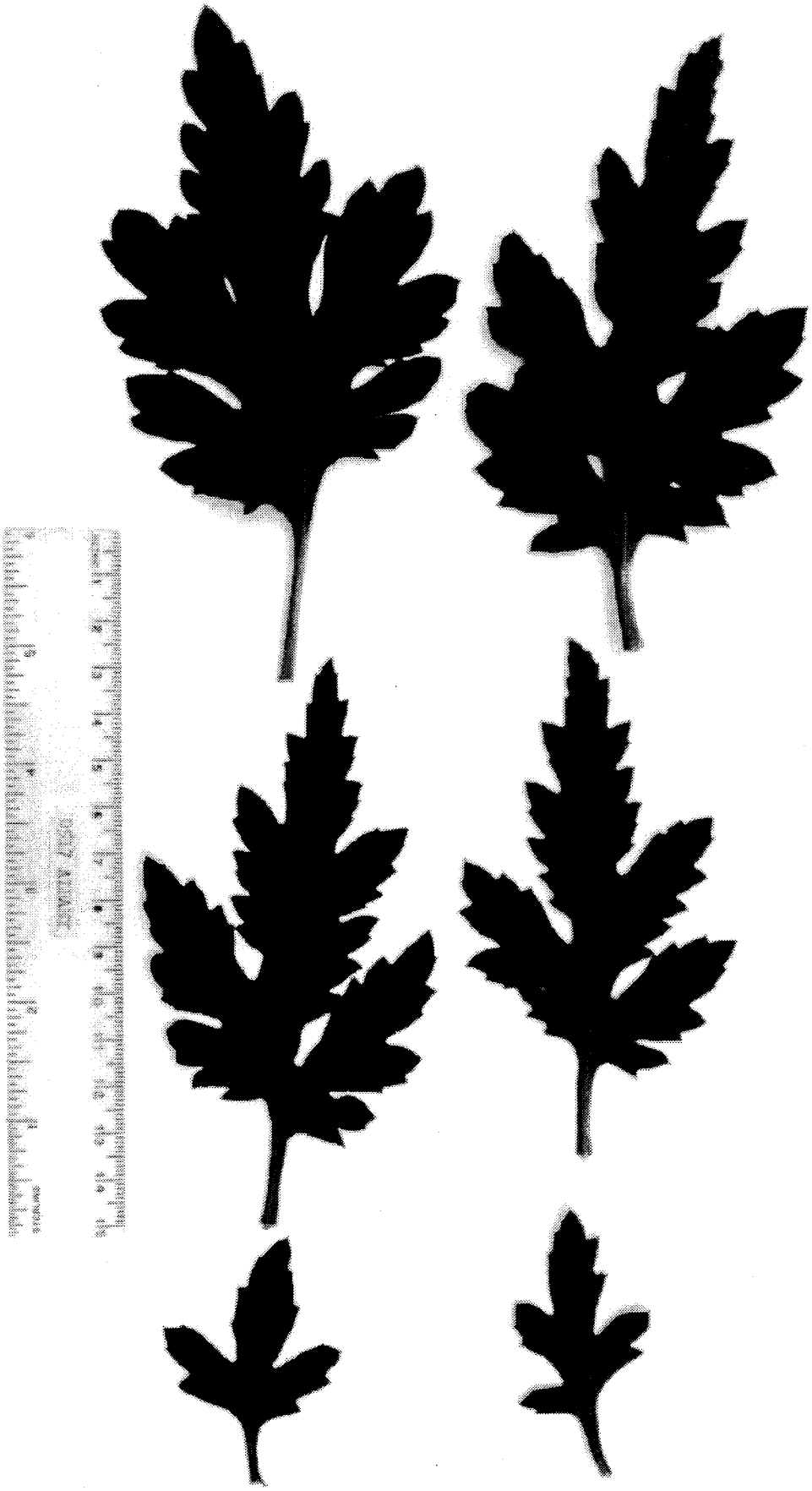

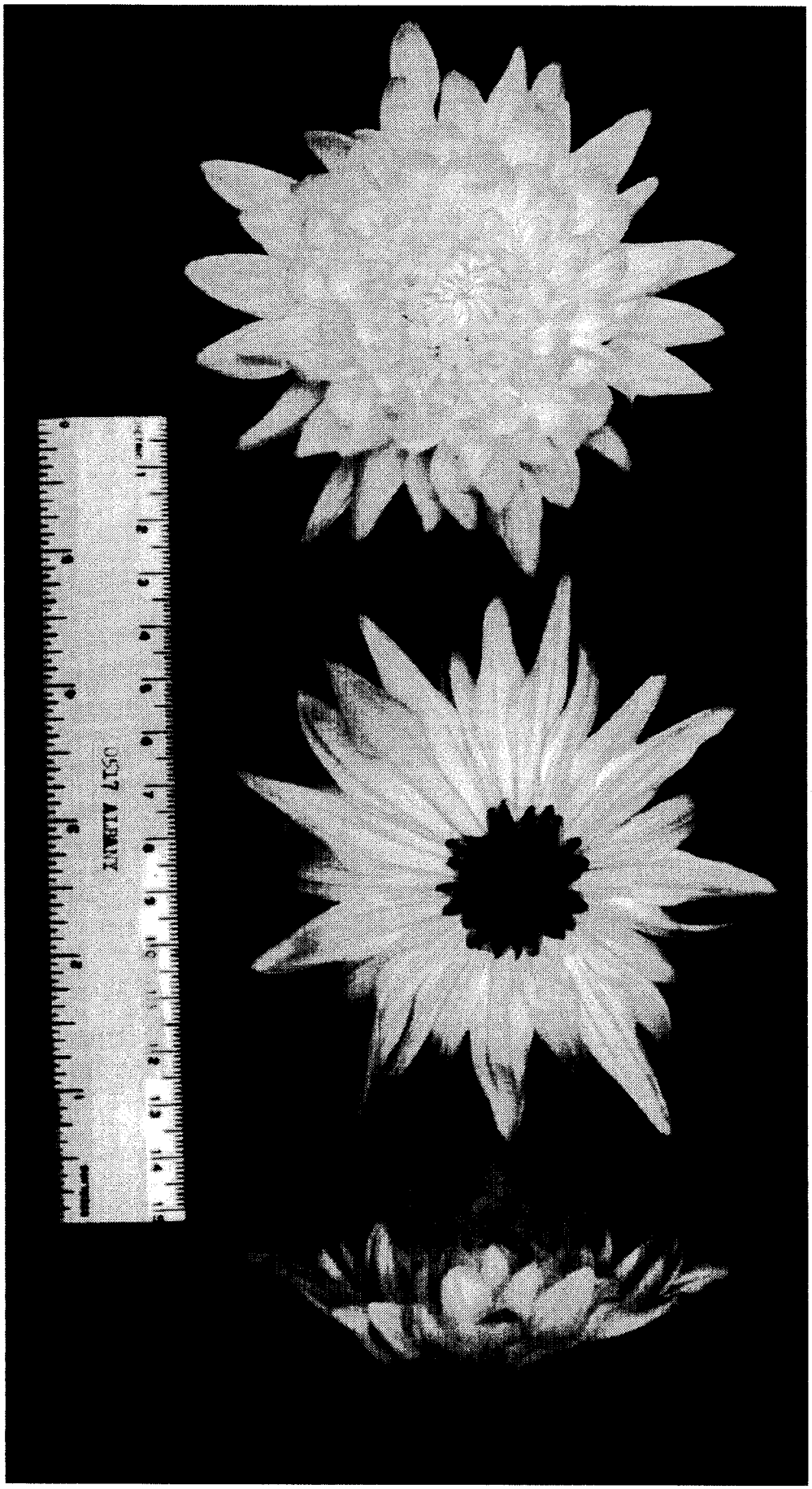
0517 ALBANY